United States Patent [19]

Pennetreau et al.

[11] Patent Number: 5,347,059
[45] Date of Patent: Sep. 13, 1994

[54] PROCESS FOR PREPARING 1,1-DICHLORO-1,3,3,3-TETRA-FLUORO-PROPANE

[75] Inventors: Pascal Pennetreau, La Hulpe; Francine Janssens, Vilvoorde; Pierre Barthelemy, Jodoigne, all of Belgium

[73] Assignee: Solvay (Société Anonyme), Brussels, Belgium

[21] Appl. No.: 182,365

[22] Filed: Jan. 18, 1994

Related U.S. Application Data

[63] Continuation of Ser. No. 910,906, Jul. 10, 1992, abandoned.

Foreign Application Priority Data

Jul. 10, 1991 [BE] Belgium ............................. 09100657

[51] Int. Cl.$^5$ ............................................. C07C 17/08
[52] U.S. Cl. ..................................... 570/166; 570/167
[58] Field of Search .................................. 570/166, 167

[56] References Cited

U.S. PATENT DOCUMENTS

| | | | |
|---|---|---|---|
| 2,452,975 | 11/1948 | Whalley | 510/168 |
| 4,091,043 | 5/1978 | Ohsaka et al. | |

FOREIGN PATENT DOCUMENTS

| | | | |
|---|---|---|---|
| 0187643 | 7/1986 | European Pat. Off. | |
| 1-269618 | 6/1968 | Fed. Rep. of Germany | |
| 2-659046 | 7/1977 | Fed. Rep. of Germany | 570/167 |
| 1319071 | 1/1963 | France | |
| 9008754 | 8/1990 | PCT Int'l Appl. | |
| 601912 | 5/1979 | U.S.S.R. | |

OTHER PUBLICATIONS

Chemical Abstracts, vol. 113, No. 1, Jul. 2nd, 1990, Columbus, OH, Abstract No. 5704U, p. 555 & JP-A-02017134.
Makromol. Chem. 185, 1583–1595 (1984).

*Primary Examiner*—Alan Siegel
*Attorney, Agent, or Firm*—Spencer, Frank & Schneider

[57] ABSTRACT

The invention relates to a process for preparing 1,1-dichloro-1,3,3,3-tetrafluoropropane by reacting, in the liquid phase, 1,1,1,3,3,3-hexachloropropane with hydrogen fluoride, in the presence of a catalyst.

8 Claims, No Drawings

PROCESS FOR PREPARING 1,1-DICHLORO-1,3,3,3-TETRA-FLUOROPROPANE

This application is a continuation application Ser. No. 07/910,906, filed Jul. 10, 1992, now abandoned.

The present invention relates to a process for preparing 1,1-dichloro-1,3,3,3-tetrafluoropropane (HFA-234fb).

It relates more particularly to a process for preparing 1,1-dichloro-1,3,3,3-tetrafluoropropane starting from 1,1,1,3,3,3-hexachloropropane, in one stage.

As a result of the problem of the depletion of the ozone layer and the restrictions consequently imposed on production and use of fully halogenated chlorofluorocarbons (CFC), there is now an increased interest in partially halogenated chlorofluorinated hydrocarbons (HFA). Among the latter, 1,1-dichloro-1,3,3,3-tetrafluoropropane could in particular prove to be an important substitute for 1,1,2-trichloro-1,2,2-trifluoroethane (CFC-113).

The subject of the inventors' certificate SU 601912 of Shvarcman et al. is the preparation of 1,1-dichloro-1,3,3,3-tetrafluoropropane, which it describes as a compound of low toxicity, which can be used as a narcotic and as an inhalation anaesthetic. 1,1-Dichloro-1,3,3,3-tetrafluoropropane is therein prepared by photochemical chlorination of 1-chloro-3,3,3-trifluoropropane, followed by fluorination of the 1,1,1-trichloro-3,3,3-trifluoropropane formed, by the action of antimony trifluoride (reactant) and in the presence of antimony pentachloride (catalyst).

This process uses as a starting material a chlorotrifluoropropane, a reactant which is already elaborate. It then requires a chlorination and a fluorination. For this last stage, antimony trifluoride is used in sizable quantities.

The aim of the present invention is to provide a process allowing preparation of 1,1-dichloro-1,3,3,3-tetrafluoropropane with good selectivity, starting from 1,1,1,3,3,3-hexachloropropane.

To this end the invention relates to a process for preparing 1,1-dichloro-1,3,3,3-tetrafluoropropane by reacting, in the liquid phase, 1,1,1,3,3,3-hexachloropropane with hydrogen fluoride, in the presence of a catalyst.

The 1,1,1,3,3,3-hexachloropropane used at the start of the process according to the invention is advantageously obtained by reacting vinylidene chloride with carbon tetrachloride.

It is thus possible to obtain 1,1-dichloro-1,3,3,3-tetrafluoropropane in two stages, starting from vinylidene chloride and carbon tetrachloride, which are simple and widely available products.

As a catalyst for the reaction in the liquid phase of 1,1,1,3,3,3-hexachloropropane with hydrogen fluoride, hydrofluorination catalysts can be used which promote the substitution of a chlorine atom by a fluorine atom. Among the catalysts which may be used, derivatives of metals, chosen from the metals of groups IIIa, IVa and b, Va and b, and VIb of the Periodic Table of the elements and their mixtures can be cited. Of special note are titanium, tantalum, molybdenum, boron, tin and antimony derivatives. Preferably, tin or antimony derivatives are used. Tin derivatives are particularly well suited. As metal derivatives, salts and more particularly halides can be cited. Preferably, the choice is made from chlorides, fluorides and chlorofluorides. Catalysts particularly preferred according to the invention are tin and antimony chlorides, fluorides and chlorofluorides and their mixtures. Chlorides are particularly well suited. Tin tetrachloride has been shown to be of particular interest, in particular in that its use results in a high selectivity for 1,1-dichloro-1,3,3,3-tetrafluoropropane.

A cocatalyst can also be used.

The quantity of catalyst used in the process can vary within wide limits. It is in general at least 0.005 mol of catalyst per mol of 1,1,1,3,3,3-hexachloropropane. Most often, it does not exceed 0.1 mol of catalyst per mol of 1,1,1,3,3,3-hexachloropropane. Preferably, it is at least 0.02 mol of catalyst per mol of 1,1,1,3,3,3-hexachloropropane. It is also preferable that it should not exceed 0.06 mol of catalyst per mol of 1,1,1,3,3,3-hexachloropropane.

The mole ratio of hydrogen fluoride to the 1,1,1,3,3,3-hexachloropropane used is in general at least 4. Most often, this mole ratio does not exceed 20. Preferably, a mole ratio of at least 6 is employed. It is also preferable that this mole ratio should not exceed 17. An excellent selectivity for 1,1-dichloro-1,3,3,3-tetrafluoropropane is obtained with a mole ratio of at least 8.

The temperature at which the reaction according to the process is carried out is in general at least 50° C. Most often, it does not exceed 150° C. Preferably, it is at least 100° C. It is also preferable that it should not exceed 120° C.

The pressure is chosen so as to keep the reaction medium in liquid form. It varies as a function of the temperature of the reaction medium. It is in general at least 2 bar. Most often, it does not exceed 50 bar. The pressure is preferably at least 10 bar. It is also preferable that it should not exceed 40 bar. It is even more preferably at least 20 bar. Excellent results are obtained without it being necessary to exceed 30 bar.

The duration of the reaction necessary to ensure an optimum selectivity for 1,1-dichloro-1,3,3,3-tetrafluoropropane varies as a function of the operating conditions and will be calculated in each case by experiments. The change in the composition of the reaction mixture can in particular be followed by quantitative analysis using gas chromatography of samples taken at regular intervals.

The process according to the invention can be carried out in any reactor made of materials which are resistant to pressure and to hydrogen fluoride. Reactors made of steel, stainless steel or alloys such as those known by the trademarks MONEL, INCONEL or HASTELLOY are often used. Reactors provided with a lining of an inert metal or alloy, or lined with a layer of a resin which is inert in the reaction conditions, in particular fluorinated resins, can also be used.

As already mentioned, the 1,1,1,3,3,3-hexachloropropane used at the start of the process according to the invention can be obtained by telomerisation of vinylidene chloride with carbon tetrachloride and in particular in the way described by Belbachir et al. (Makromol. Chem., 185, 1984, 1583–1595).

This reaction is advantageously carried out in the presence of a catalyst of the peroxide or iron or copper salt type and, in particular, cuprous chloride, which gives an excellent selectivity for the 1,1,1,3,3,3-hexachloropropane produced.

The said reaction is moreover advantageously carried out in the presence of a polar solvent which is a donor, such as dimethyl sulphoxide or acetonitrile, acetonitrile giving excellent results.

EXAMPLE 1 a. Preparation of 1,1,1,3,3,3-hexachloropropane

A 1-l autoclave lined with a TEFLON ® fluorocarbon resin, fitted with a stirrer, a temperature probe and a dip pipe allowing samples to be taken during the trials is used.

1.8 mol of vinylidene chloride, 3.6 mol of carbon tetrachloride, 0.018 mol of cuprous chloride and 3.6 mol of acetonitrile are introduced into this autoclave.

The reaction mixture is stirred and heated to 140° C. for 13 hours. The autogenous pressure reaches 5.9 bar.

The autoclave is then cooled to room temperature and is emptied.

Analysis shows that the conversion vinylidene chloride is then 95 mol % and the selectivity for 1,1,1,3,3,3-hexachloropropane is 87 mol % in relation to the vinylidene chloride converted.

The 1,1,1,3,3,3-hexachloropropane obtained is purified by distillation under reduced pressure.

b. Hydrofluorination of 1,1,1,3,3,3-hexachloropropane

A 0.5-l stainless steel autoclave, fitted with a stirrer, a pressure regulating system, a temperature probe and a dip pipe allowing samples to be taken during the trials is used.

This reactor is evacuated and cooled to −20° C.

0.4 mol of 1,1,1,3,3,3-hexachloropropane, 0.02 mol of tin tetrachloride and 3.6 mol of hydrogen fluoride are introduced into it in succession.

The reaction mixture is then progressively heated to 110° C. and the pressure is regulated at 25 bar.

After 45 hours, the conversion of 1,1,1,3,3,3-hexachloropropane is 100% and the overall selectivity for 1,1-dichloro-1,3,3,3-tetrafluoropropane is 50 mol % in relation to the 1,1,1,3,3,3-hexachloropropane converted. After 115 hours this selectivity reaches 79%.

At the end of the reaction, the mixture is cooled and poured into a polyethylene separating funnel filled with water, so as to separate off the hydrogen fluoride which has not reacted. The organic phase is separated off and 1,1-dichloro-1,3,3,3-tetrafluoropropane is purified by distillation.

EXAMPLE 2

The procedure is similar to that of Example 1.

0.4 mol of 1,1,1,3,3,3-hexachloropropane, 0.02 mol of antimony pentachloride and 3.2 mol of hydrogen fluoride are introduced in succession into the reactor.

The reaction mixture is then progressively heated to 110° C. and the pressure is regulated at 25 bar.

The reaction is very fast.

After 6 hours, the conversion of 1,1,1,3,3,3-hexachloropropane is 100% and the selectivity for 1,1-dichloro-1,3,3,3-tetrafluoropropane is more than 40 mol % in relation to the 1,1,1,3,3,3-hexachloropropane converted.

We claim:

1. A process for preparing 1,1-dichloro-1,3,3,3-tetrafluoropropane, comprising:

reacting 1,1,1,3,3,3-hexachloropropane in the liquid phase with hydrogen fluoride, in a mole ratio of hydrogen fluoride to 1,1,1,3,3,3-hexachloropropane of at least 4 and not exceed more than 20, at a reaction temperature of at least about 100° C. and not more than about 150° C., and in the presence of a tin tetrachloride catalyst to produce 1,1-dichloro-1,3,3,3-tetrafluoropropane; and recovering said 1,1-dichloro-1,3,3,3-tetrafluoropropane.

2. The process according to claim 1, wherein the tin tetrachloride catalyst is used in a ratio of 0.005 to 0.1 mol of catalyst per mol of 1,1,1,3,3,3-hexachloropropane.

3. The process according to claim 1, wherein the mole ratio of hydrogen fluoride to the 1,1,1,3,3,3-hexachloropropane used is at least 6 and does not exceed 17.

4. The process according to claim 1, wherein the reaction is carried out at a pressure of at least 2 bar and not more than 50 bar.

5. The process according to claim 4, wherein the pressure at which the reaction is carried out is at least 10 bar.

6. The process according to claim 1, wherein the catalyst is used in a ratio of about 0.02 to 0.06 mol of catalyst per mol of 1,1,1,3,3,3-hexachloropropane.

7. The process according to claim 1, wherein a mole ratio of hydrogen fluoride to 1,1,1,3,3,3-hexachloropropane used is at least 8 and does not exceed 17.

8. The process according to claim 1, wherein the reaction is carried out at a pressure of at least 20 bar and not more than 30 bar.

* * * * *

Before its use in the process according to the invention, the 1,1,1,3,3,3-hexachloropropane can be purified, in particular by distillation under reduced pressure.

The examples which follow are given with the aim of illustrating the invention but are in no way limiting.